United States Patent [19]

Toomey

[11] Patent Number: 5,247,093
[45] Date of Patent: Sep. 21, 1993

[54] CHLORINATION PROCESS

[75] Inventor: Joseph E. Toomey, Indianapolis, Ind.

[73] Assignee: Reilly Industries, Inc., Indianapolis, Ind.

[21] Appl. No.: 990,904

[22] Filed: Dec. 15, 1992

[51] Int. Cl.⁵ ................ C07D 213/127; C07D 213/61
[52] U.S. Cl. .................................... 546/345; 546/346
[58] Field of Search ............................... 546/345, 346

[56] References Cited

U.S. PATENT DOCUMENTS 2,839,534  8/1956  Shrader et al.
3,153,044 10/1964  Zaslowsky.
3,251,848  5/1966  Taplin, III et al. ................. 546/345
3,412,095 11/1968  Clark.
4,054,499 10/1977  Kawamura et al.

FOREIGN PATENT DOCUMENTS 1097678  8/1964  United Kingdom.

Primary Examiner—C. Warren Ivy
Assistant Examiner—D. Margaret M. Mach
Attorney, Agent, or Firm—Woodard, Emhardt, Naughton, Moriarty & McNett

[57] ABSTRACT

A process for the selective chlorination of pyridine or a lower alkyl pyridine includes passing the pyridine compound, chlorine and an inert gas through a two stage reaction. In a first reaction zone, these materials are subjected to a hot spot controlled at a temperature of about 350° to about 500° C. The materials are then subsequently passed through a second reaction zone at a relatively lower temperature, for example below about 340° C.

20 Claims, No Drawings

CHLORINATION PROCESS

BACKGROUND

The present invention generally relates to a method for selectively chlorinating pyridine or an alkyl pyridine, and more particularly to such a method conducted in the gas phase in the presence of chlorine as the chlorinating agent.

Chlorinated pyridine derivatives have been prepared by a variety of techniques. One general approach to preparing chlorinated pyridines involves the chlorination of pyridine or of a pyridine derivative with molecular chlorine used as the chlorinating agent ($Cl_2$, hereinafter referred to as "chlorine"). A number of differing techniques for chlorinating pyridine or its derivatives with chlorine have been developed.

In one facet, thermally-induced chlorinations have been conducted in the vapor phase in a reactor maintained at a generally uniformly high temperature, generally above 250° C. and even 300° to 400° C., as has generally been described in U.S. Pat. Nos. 2,820,791 and 3,153,044 These methods have in the past presented various disadvantages such as poor selectivity and substantial formation of tars that clog the reactor or associated pipes, making a continuous operation difficult.

Another chlorination route involves reactions that are initiated by means of light or ultra-violet rays. Such methods have been described, for example, in U.S. Pat. Nos. 3,297,556 and 4,054,499. These methods, although they can be operated at temperatures lower than thermally-induced methods, have lead to the deleterious formation of tarry by-products that foul the light tubes and give rise to a corresponding reduction in the initiation radiation, and hence in the efficiency of the overall reaction or process.

Still other chlorination routes involve the use of chemical compounds that initiate the chlorination reaction, either in liquid or in vapor phase. While providing enhanced selectivities, particularly in the gas phase, these routes nevertheless require the use of the chemical initiators to achieve acceptable process results.

In light of this background, there remains a need and demand for processes for the chlorination of pyridine or alkyl pyridines which provide high selectivities and acceptable yields and conversions. The present invention addresses this need.

SUMMARY OF THE INVENTION

The present invention relates to the applicant's discovery that the controlled generation of an isolated hot spot within a chlorination reaction zone of generally lower temperature surprisingly leads to unexpected increases in the selectivity of the chlorination of pyridine or alkyl pyridines. Thus, one preferred embodiment of the invention provides a process for selectively chlorinating pyridine or a lower alkyl pyridine. The inventive process includes the step of passing a vaporized feed stream including pyridine or lower alkyl pyridine, chlorine and an inert gas into a first reaction zone having a hot spot controlled at a temperature of about 350° C. to about 500° C., and subsequently through a second reaction zone at a temperature below about 340° C. Surprisingly, by this method, chlorination processes of highly improved selectivity are obtained, for example as compared to similar chlorinations conducted in a reactor having a single controlled temperature reaction zone. Additionally, good yields and conversions are obtained by the process, with significantly less tarring than would be obtained using a single reaction zone entirely maintained at the hot spot temperature. As further advantages, the reaction can conveniently be conducted in a tubular reactor, preferably vertically oriented with the reactant feed into the top of the reactor. Moreover, the high selectivities are achieved without the need for using chemical additives for initiation of the reaction as in some prior processes.

These and other objects, advantages and features of the invention will be apparent upon reviewing the following description and the appended claims.

DESCRIPTION OF THE PREFERRED EMBODIMENT

For the purpose of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention illustrated herein being contemplated as would normally occur to one skilled in the art to which the invention relates.

As indicated above, one preferred embodiment of this invention relates to a process for selectively chlorinating pyridine or a lower alkyl pyridine. In this regard, as used herein, the term "lower alkyl" means a branched or unbranched alkyl group having from 1 to about 5 carbon atoms, e.g. methyl, ethyl, propyl, isopropyl, butyl, isobutyl, etc. Particularly preferred chlorinations of the present invention provide for the chlorination of pyridine to form 2-chloropyridine, and the chlorination of 2-picoline and 3-picoline to form predominantly their corresponding (2- or 3-)chloromethylpyridines and (2- or 3-)dichloromethylpyridines.

In conducting processes according to the present invention, the chlorine and the pyridine or alkyl pyridine, which may be of synthetic or natural origin, are usually included in the reactant feed in molar ratios of about 0.1 to about 20 moles of chlorine per mole of pyridine compound. This ratio depends in particular on the number of hydrogen atoms that are to be substituted with chlorine in the process at hand. More preferably, this ratio ranges between about 0.2 and about 15 moles, and most preferably between about 0.3 and about 10 moles of chlorine per mole of pyridine compound. In the preferred selective production of 2-chloropyridine by chlorination of pyridine, this molar ratio advantageously lies between about 0.2 moles and about 2 moles of chlorine per mole of pyridine. When chlorinating a lower alkyl pyridine by the inventive process, the preferred ratio lies between about 2 and about 20 moles of chlorine per mole of alkyl pyridine involved in the reaction.

Aside from the reactants mentioned above, it is advantageous to make use, in the method according to the invention, of inert gas additives such as water vapor, nitrogen and/or other inert gases which do not participate in the chlorination reaction. Highly desirable chlorination reactions are conducted in the presence of water vapor provided at a level of about 0.1 to about 25 moles per mole of pyridine compound involved. More preferably, water vapor quantities of about 1 to about 15 moles per mole of pyridine compound are employed. Although the water vapor or other inert gas may be provided to the reactor in any suitable fashion, water vapor is advantageously supplied by premixing water and the pyridine compound involved, passing this mixture into an evaporator, and then passing the vapors thus obtained into the chlorination reaction zone.

As will be readily understood and appreciated by those experienced in the field, it may also be desirable in some instances to conduct the chlorination reaction in the presence of additives acting as diluents, but inert with respect to the chlorination reaction. These diluents are included in order to minimize the superheating of the reaction mixture and to avoid the condensation of reaction products of low volatility. Suitable such additives include chlorine-containing derivatives of aliphatic compounds such as carbon tetrachloride or inorganic products such as hydrogen chloride or nitrogen, although many others will also be acceptable and used by practiced artisans without need for resort to any undue experimentation.

In the process of the invention, a vaporized feed stream including the pyridine compound, chlorine and inert gas is passed into a first reaction zone that includes a hot spot controlled at a temperature of about 350° C. to about 500° C. This hot spot may be thermally produced, for example, by communicating heat into the reaction zone by a heat source exterior of the reactor. More preferably in the present invention, the hot spot is controlled at a temperature of about 360° to about 470° C., and most preferably about 360° C. to about 420° C. The hot spot of most advantageous temperature for a particular reaction will depend upon several factors such as the specific reactants and inert diluents involved, the flow rate of materials through the hot spot, and the like. Controlling and accounting for these and similar parameters in achieving most beneficial hot spot temperatures will readily be accomplished by those who work in the area.

Subsequent to contacting the feed stream materials with the hot spot reaction zone, the materials are passed into a second reaction zone at a temperature relatively lower than that of the hot spot. For example, this second reaction zone temperature in the applicant s work thus far has advantageously been below about 340° C., preferably in the range of about 100° C. to about 340° C., and more preferably in the range of about 200° to about 340° C. Again, selection and use of most beneficial temperatures in this second reaction zone will pose no undue burden upon the skilled artisan.

It is preferred that the feed stream residence time in the hot spot reaction zone be shorter than its residence time in the second, lower-temperature reaction zone. For example, residence times of about 2 seconds or less are desirable in the hot spot reaction zone, while residence times in the second reaction zone may be longer, for instance several minutes, but are usually up to about 30 seconds, preferably about 5 to about 10 seconds.

After the chlorination is complete, the chlorinated product or products can be recovered and isolated in a conventional fashion. For example, the crude reaction product can be treated with a basic material and extracted, for instance with chloroform or another similar extracting agent. Further purification and recovery steps, e.g. distillation, etc. will be conventionally employed if desired.

The chlorinated pyridine products obtained by the process of the present invention are suitably employed as chemical intermediates in the manufacture, for example, of products used in agriculture, cosmetics and the pharmaceutical industry.

For the purposes of promoting a further understanding of the present invention and its preferred features and embodiments, the following examples are being provided. It will be understood, however, that these examples are illustrative, and not limiting, in nature.

EXAMPLES 1-11

Chlorinations of Pyridine

A chlorination reactor for use in the present invention was constructed as follows. A quartz tube having a length of 45 cm and a diameter of 2 cm was vertically oriented. Above and directly connected to the tube was a feed mixing manifold constructed of PYREX. The feed mixing manifold contained a central thermowell inlet, two gas feed ports and a liquid feed nozzle. Nitrogen gas and chlorine gas, and all liquid feed to the reactor could be fed separately and independently of each other. Preheating was provided in the manifold by an external heat source. In all runs, the preheated area was maintained between about 100° C. and 200° C.

A hot spot was created at the top of the quartz tube by means of beaded heat tape. The hot spot length on the tube was from about 2 to 4 cm. The remainder of the tube was heated with a tube oven. A receiver was connected at the bottom of the reactor tube. Materials were fed to the manifold at a rate that gave residence times between 6 and 9 seconds through the entire 45 cm tube. The molar ratio of chlorine to pyridine was 1-2:1 and for water to pyridine it was 8:1.

For product analysis, the crude acidic mixture exiting the reactor was collected in the receiver at the bottom of the reactor tube. The crude material was made basic and extracted with chloroform. GC analysis of the combined organic extract gave the weight percent of each component.

Eleven chlorination runs were conducted under varying temperature conditions in the two reaction zones of the reactor. Also, varying pyridine sources were employed. After analysis of the product, the conversion of pyridine, yield of 2-chloropyridine and 2,6-dichloropyridine, and the selectivities for these two chlorinated products were determined. The results are set forth in Table 1 below, in which the designation "NA" means not assayed.

TABLE 1

| Ex. | Temp. (°C.) Hot Spot Zone | Temp. (°C.) Second Zone | Pyridine Source | Conversion | Yield (%) 2-Cl Pyr | Yield (%) 2,6-diCl Pyr | Select (%) 2-Cl Pyr | Select (%) 2,6-diCl Pyr |
|---|---|---|---|---|---|---|---|---|
| 1 | 168 | 224 | Spec[a] | 3.1 | 5.3 | 0.1 | NA | 1.8 |
| 2 | 220 | 240 | Spec | 0 | 7.0 | 0.1 | NA | NA |
| 3 | 283 | 248 | Spec | 9.8 | 13.7 | 0.5 | NA | 5.3 |
| 4 | 357 | 130 | 1 degree[b] | 25.2 | 18.4 | 0.7 | 73.2 | 3.0 |
| 5 | 367 | 335 | 1 degree | 33.5 | 34.4 | 1.8 | 102.4 | 5.4 |
| 6 | 393 | 169 | 1 degree | 41.9 | 27.3 | 1.3 | 65.2 | 3.2 |
| 7 | 393 | 269 | Spec | 32.5 | 29.7 | 1.0 | 91.5 | 3.1 |

TABLE 1-continued

| Ex. | Temp. (°C.) Hot Spot Zone | Temp. (°C.) Second Zone | Pyridine Source | Conversion | Yield (%) 2-Cl Pyr | Yield (%) 2,6-diCl Pyr | Select (%) 2-Cl Pyr | Select (%) 2,6-diCl Pyr |
|---|---|---|---|---|---|---|---|---|
| 8 | 396 | 190 | Spec | 49.1 | 31.9 | 1.5 | 65.0 | 3.1 |
| 9 | 397 | 271 | Spec | 31.5 | 32.0 | 1.5 | 101.6 | 4.8 |
| 10 | 469 | 290 | Spec | 57.1 | 41.7 | 2.4 | 72.9 | 4.1 |
| 11 | 589 | 188 | Spec | 56.1 | 11.6 | 0.8 | 20.6 | 1.4 |

*"Spec" = Spec. grade pyridine as available from Reilly Industries, Inc. Indianapolis, Indiana.
*"1 degree" = pyridine distilling within 1 degree, commercially available from Reilly Industries, Inc.

As the data in Table 1 shows, a hot spot reaction zone can be advantageously employed to achieve high selectivity for 2-chloropyridine with good yields and conversions. In the applicant's work, the advantageous results were obtained using a hot spot of about 350° C. to about 500° C. At temperatures substantially above 500° C., e.g. in run 11 with a hot spot of 589° C., conversions of pyridine are high; however, yields of and selectivities for 2-chloropyridine are very low. On the other hand, using hot spot temperatures substantially below about 360° C., e.g. as in runs 1, 2 and 3 in which respective hot spot temperatures of 283° C., 220° C. and 168° C. were used, conversions are very poor as are yields of 2-chloropyridine. In contrast, in runs in which a hot spot temperature between about 350° C. and about 500° C. were used, conversions were good, yields of 2-chloropyridine were good, and selectivities for 2-chloropyridine were good. For instance, in Examples 5, 6, 7 and 9, in which the hot spot temperature ranged between about 360° C. and about 400° C., conversions ranged between 30 percent and 42 percent, while selectivities for 2-chloropyridine were between 90 percent and 100 percent. This advantageous combination of conversions/yields/selectivities for 2-chloropyridine is highly unexpected and highlights the dramatic nature of the applicant's discovery.

While some material balance inconsistencies exist in some of the reported runs, they are minor. These inconsistencies are based upon slight experimental and analytical errors inherent in the system, and the reported runs nevertheless represent solid and reproducible examples of processes of the invention.

EXAMPLES 12-13

Chlorinations of 3-Picoline

3-Picoline was chlorinated with (Example 12) and without (Example 13) the use of a hot spot as in the invention. Thus, using the reactor previously described in connection with Examples 1-11, 3-picoline was chlorinated using a hot spot temperature of 350° C., and a second reaction zone temperature of 200° C. For this run, the molar feed ratio of chlorine to 3-picoline was 7.4, and this ratio of water to 3-picoline was 8.0. Total residence time in the reactor was 6.1 seconds. The predominant products were 3-chloromethylpyridine and 3-dichloromethylpyridine, which were recovered in respective yields of 17.9 percent and 12.1 percent. The conversion of 3-picoline in this run was 90%. In another run, 3-picoline was chlorinated employing a "hot spot" temperature of 200° C. and a second reaction zone temperature of 200° C. The molar feed ratio of chlorine to 3-picoline was 8.1, and the ratio of water to 3-picoline was 8.0. Total residence time in the reactor was 6.3 seconds. In this run, conversion of 3-picoline was only 61 percent and the predominant product was 3-chloromethylpyridine, which was recovered in 19.1 percent yield. These runs demonstrate that a hot spot as used in the present invention provides superior conversion while yielding predominantly both 3-chloromethylpyridine and 3-dichloromethylpyridine.

EXAMPLE 14-15

Chlorinations of 2-Picoline

Using the above-described reactor, 2-picoline was chlorinated with (Example 14) and without (Example 15) the use of a hot spot as provided by the present invention. Thus, in one run, 2-picoline was chlorinated using a hot spot temperature of 350° C. and a second reaction zone temperature of 200° C. The molar ratio of chlorine to 2-picoline was 7.5, and the molar ratio of water to 2-picoline was 8.1. Residence time (total) in the reactor was 6.5 seconds. Similar to Examples 12, the predominant products were the corresponding chloromethylpyridine and dichloromethylpyridine, i.e. 2-chloromethylpyridine and 2-dichloromethylpyridine (representing 15.3 and 10.7 GC area % of the products, respectively). In another run (Example 15), 2-picoline was chlorinated without using a hot spot as in the invention. Thus, 2-picoline was chlorinated using a "hot spot" temperature of 200° C., and a second reaction zone temperature of 200° C. The molar ratios of chlorine to 2-picoline and water to 2-picoline were 7.0 and 8.0, respectively. Total residence time in the reactor was 7.1 seconds. Again, conversion was significantly reduced as compared to the corresponding hot spot run. The predominant product was 2-chloromethylpyridine, which registered 11.9 GC area %. 2-Picoline and 2-dichloromethylpyridine registered at 13.6 and 3.3 GC area %, respectively.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What I claim is:

1. A process for selectively chlorinating pyridine or a lower alkyl pyridine, comprising:
    passing a vaporized feed stream including pyridine or lower alkyl pyridine, chlorine and an inert gas into a first reaction zone having a hot spot controlled at a temperature of at about 350° C. to about 500° C., and subsequently through a second reaction zone at a temperature below about 340° C.

2. The process of claim 1 wherein the vaporized feed stream includes pyridine.

3. The process of claim 1 wherein the vaporized feed stream includes lower alkyl pyridine.

4. The process of claim 3 wherein the lower alkyl pyridine is beta-picoline.

5. The process of claim 1 wherein the first reaction zone has a hot spot controlled at a temperature of about 360° C. to about 470° C.

6. The process of claim 1 wherein the first reaction zone has a hot spot controlled at a temperature of about 360° C. to about 420° C.

7. The process of claim 1 wherein the second reaction zone is at a temperature above about 100° C.

8. The process of claim 1 wherein the second reaction zone is at a temperature above about 200° C.

9. The process of claim 6 wherein the second reaction zone is at a temperature above about 100° C.

10. The process of claim 6 wherein the second reaction zone is at a temperature above about 200° C.

11. The process of claim 1 wherein the inert gas is water vapor.

12. The process of claim 10 wherein the inert gas is water vapor.

13. The process of claim 12 wherein the feed stream includes pyridine so as to selectively produce 2-chloropyridine.

14. The process of claim 12 wherein the feed stream includes beta-picoline so as to selectively produce 2-chloro-5-trichloromethyl pyridine.

15. A process for selectively producing 2-chloropyridine by chlorination of pyridine with chlorine, comprising:

passing a vaporized feed stream including pyridine, chlorine and an inert gas into a first reaction zone having a hot spot at a temperature of about 350° C. to about 420° C., and subsequently passing the stream through a second reaction zone having a temperature of about 200° C. to about 340° C., so as to selectively produce 2-chloropyridine.

16. The process of claim 15 wherein the residence time of said feed stream in said first reaction zone is about 2 seconds or less.

17. The process of claim 16 wherein said residence time is about 1 second or less.

18. The process of claim 15 wherein said inert gas is water vapor.

19. The process of claim 18 wherein the molar ratio of chlorine to pyridine in said feed stream is about 0.2-2:1.

20. The process of claim 19 wherein said molar ratio is about 1-2:1.

* * * * *